United States Patent
Zuo et al.

(10) Patent No.: US 10,585,082 B2
(45) Date of Patent: Mar. 10, 2020

(54) DOWNHOLE FILTRATE CONTAMINATION MONITORING

(71) Applicant: Schlumberger Technology Corporation, Sugar Land, TX (US)

(72) Inventors: Youxiang Zuo, Burnaby (CA); Kang Wang, Beijing (CN); Adriaan Gisolf, Houston, TX (US); Ryan Sangjun Lee, Sugar Land, TX (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 688 days.

(21) Appl. No.: 15/135,411

(22) Filed: Apr. 21, 2016

(65) Prior Publication Data

US 2016/0319662 A1  Nov. 3, 2016

Related U.S. Application Data

(60) Provisional application No. 62/155,306, filed on Apr. 30, 2015.

(51) Int. Cl.
*G01N 33/28* (2006.01)
*E21B 49/10* (2006.01)
(Continued)

(52) U.S. Cl.
CPC ......... *G01N 33/2823* (2013.01); *E21B 49/10* (2013.01); *G01F 22/00* (2013.01); *G01N 9/36* (2013.01)

(58) Field of Classification Search
CPC ...... E21B 49/08; E21B 49/087; E21B 49/088; E21B 49/10; E21B 2049/085;
(Continued)

(56) References Cited

U.S. PATENT DOCUMENTS

| | | | | |
|---|---|---|---|---|
| 8,555,968 | B2* | 10/2013 | Zazovsky | E21B 49/008 166/100 |
| 2003/0217845 | A1* | 11/2003 | Sherwood | E21B 49/10 166/264 |

(Continued)

OTHER PUBLICATIONS

Zuo et al. "A Breakthrough in Accurate Downhole Fluid Sample Contamination Prediction in Real Time," Petrophysics, vol. 56, No. 3 (Jun. 2015); p. 251-265.

(Continued)

*Primary Examiner* — Daniel S Larkin
*Assistant Examiner* — Anthony W Megna Fuentes
(74) *Attorney, Agent, or Firm* — Trevor G. Grove

(57) ABSTRACT

A method includes operating a downhole acquisition tool in a wellbore in a geological formation. The wellbore or the geological formation, or both, contains first fluid that includes a native reservoir fluid of the geological formation and a contaminant. The method also includes receiving a portion of the first fluid into the downhole acquisition tool and determining a plurality of properties of the portion of the first fluid using the downhole acquisition tool. The plurality of properties includes a mass fraction of a component of the portion of the first fluid and a density of the portion of the first fluid. The method also includes using the processor to estimate a volume fraction of the contaminant in the portion of the first fluid based at least in part on a composition mass fraction function that depends at least on the mass fraction of the component in the portion of the first fluid and the density of the portion of the first fluid.

20 Claims, 8 Drawing Sheets

(51) Int. Cl.
*G01N 9/36* (2006.01)
*G01F 22/00* (2006.01)

(58) Field of Classification Search
CPC .............. G01N 21/8507; G01N 21/94; G01N 33/2823; G01N 2021/855; G01V 8/10
USPC .............. 73/152.18, 152.23–152.26, 152.28
See application file for complete search history.

(56) References Cited

U.S. PATENT DOCUMENTS

| | | | | |
|---|---|---|---|---|
| 2004/0000433 A1* | 1/2004 | Hill | ........................ | E21B 49/08 175/59 |
| 2006/0000603 A1* | 1/2006 | Zazovsky | ............... | E21B 49/08 166/244.1 |
| 2006/0076132 A1* | 4/2006 | Nold, III | ................. | E21B 49/10 166/264 |
| 2006/0117842 A1* | 6/2006 | Ramakrishnan | ........ | E21B 49/10 73/152.55 |
| 2007/0119244 A1* | 5/2007 | Goodwin | ................ | E21B 47/10 73/152.28 |
| 2008/0073078 A1* | 3/2008 | Sherwood | ............... | E21B 49/10 166/264 |
| 2008/0125973 A1* | 5/2008 | Sherwood | ............... | E21B 49/10 702/11 |
| 2009/0314077 A1* | 12/2009 | Tustin | ..................... | E21B 49/10 73/152.24 |
| 2010/0175873 A1* | 7/2010 | Milkovisch | ........... | E21B 49/008 166/264 |
| 2011/0088949 A1* | 4/2011 | Zuo | ........................ | E21B 49/08 175/48 |
| 2011/0284219 A1* | 11/2011 | Pomerantz | .............. | E21B 49/10 166/264 |
| 2011/0284227 A1* | 11/2011 | Ayan | ....................... | E21B 43/16 166/307 |
| 2012/0132419 A1* | 5/2012 | Zazovsky | ............. | E21B 49/008 166/264 |
| 2012/0232799 A1* | 9/2012 | Zuo | ........................ | E21B 49/00 702/6 |
| 2012/0296617 A1* | 11/2012 | Zuo | ........................ | E21B 47/10 703/10 |
| 2013/0151159 A1* | 6/2013 | Pomerantz | ............ | E21B 49/082 702/11 |
| 2014/0316705 A1 | 10/2014 | Zuo et al. | | |
| 2015/0142317 A1 | 5/2015 | Zuo et al. | | |
| 2015/0211361 A1 | 7/2015 | Gisolf et al. | | |
| 2015/0226059 A1 | 8/2015 | Zuo et al. | | |
| 2015/0292324 A1 | 10/2015 | Jackson et al. | | |
| 2015/0308261 A1 | 10/2015 | Zuo et al. | | |
| 2015/0308264 A1 | 10/2015 | Zuo et al. | | |
| 2016/0061743 A1 | 3/2016 | Wang | | |

OTHER PUBLICATIONS

Zuo et al. "Quantitative mixing rules for downhole oil-based mud contamination monitoring in real time using multiple sensors," Journal of Petroleum Science and Engineering, 137, (2016), pp. 214-226.

U.S. Appl. No. 14/534,813, filed Nov. 6, 2014.

* cited by examiner

DOWNHOLE FILTRATE CONTAMINATION MONITORING

CROSS-REFERENCE TO RELATED APPLICATIONS

This application claims benefit of U.S. Provisional Patent Application Ser. No. 62/155,306, filed Apr. 30, 2015, which is herein incorporated by reference.

BACKGROUND

This disclosure relates to determining drilling mud contamination of native formation fluids downhole.

This section is intended to introduce the reader to various aspects of art that may be related to various aspects of the present techniques, which are described and/or claimed below. This discussion is believed to be helpful in providing the reader with background information to facilitate a better understanding of the various aspects of the present disclosure. Accordingly, it should be understood that these statements are to be read in this light, and not as an admission of any kind.

Fluid sampling may be used in a wellbore in a geological formation to locate hydrocarbon-producing regions in the geological formation, as well as to manage production of the hydrocarbons in these regions. As such, formation fluid (e.g., drilling mud contaminated formation fluid or uncontaminated (native) formation fluid) that is generally of greatest interest for sampling or testing is the native reservoir fluid (e.g., water, gas, oil, etc.). To sample or test the formation fluid, a downhole acquisition tool may be moved into the wellbore to draw in the fluid.

Fluids other than the native reservoir fluid may contaminate the native reservoir fluid. Drilling muds, for example, may be used in drilling operations to mechanically power rotation of a drill bit and help remove rock cuttings out of the wellbore. The fluid drawn from the wellbore thus may be a mixture of native reservoir fluid and drilling mud filtrate. Of certain concern are oil-based mud drilling fluids that may be miscible with certain native reservoir fluids (e.g., oil and gas). The miscibility of the oil-based mud and the reservoir fluid may cause difficulties in evaluation of the reservoir fluid for assessing the hydrocarbon regions, in particular the region's economic value.

SUMMARY

This summary is provided to introduce a selection of concepts that are further described below in the detailed description. This summary is not intended to identify key or essential features of the subject matter described herein, nor is it intended to be used as an aid in limiting the scope of the subject matter described herein. Indeed, this disclosure may encompass a variety of aspects that may not be set forth below.

In one example, a method includes operating a downhole acquisition tool in a wellbore in a geological formation. The wellbore or the geological formation, or both, contains a first fluid that includes a native reservoir fluid of the geological formation and a contaminant. The method also includes receiving a portion of the first fluid into the downhole acquisition tool and determining a plurality of properties of the portion of the first fluid using the downhole acquisition tool. The plurality of properties includes a mass fraction of a component of the portion of the first fluid and a density of the portion of the first fluid. The method also includes using the processor to estimate a volume fraction of the contaminant in the portion of the first fluid based at least in part on a composition mass fraction function that depends at least on the mass fraction of the component in the portion of the first fluid and the density of the portion of the first fluid.

In another example, a downhole fluid testing system includes a downhole acquisition tool housing that may be moved into a wellbore in a geological formation. The wellbore or the geological formation, or both, contains a first fluid that includes a native reservoir fluid of the geological formation and a contaminant. The downhole fluid testing system also includes a plurality of sensors disposed in the downhole acquisition tool housing that may analyze portions of the first fluid and obtain sets of properties of the portions of the first fluid. Each set of properties includes a mass fraction of a component of the portion of the first fluid and a density of the portion of the first fluid. The downhole fluid testing system also includes a data processing system that may estimate a volume fraction of the contaminant in at least one of the portions of the first fluid based at least in part on a composition mass fraction function that depends at least on the mass fraction of the component the at least one portion of the first fluid and the density of the at least one portion of the first fluid.

In another example, one or more tangible, non-transitory, machine-readable media including instructions to receive a plurality of fluid parameters of a portion of first fluid as analyzed by a downhole acquisition tool in a wellbore in a geological formation. The wellbore or the geological formation, or both, contains the first fluid, the first fluid includes a mixture of native reservoir fluid of the geological formation and a contaminant, and the plurality of fluid parameters includes a mass fraction of a component of the portion of the first fluid and a density of the portion of the first fluid. The one or more tangible, non-transitory, machine-readable media also includes instructions to estimate a volume fraction of the contaminant in the portion of the first fluid based at least in part on a composition mass fraction function that depends at least on the mass fraction of the component in the portion of the first fluid and the density of the portion of the first fluid.

Various refinements of the features noted above may be undertaken in relation to various aspects of the present disclosure. Further features may also be incorporated in these various aspects as well. These refinements and additional features may exist individually or in any combination. For instance, various features discussed below in relation to one or more of the illustrated embodiments may be incorporated into any of the above-described aspects of the present disclosure alone or in any combination. The brief summary presented above is intended to familiarize the reader with certain aspects and contexts of embodiments of the present disclosure without limitation to the claimed subject matter.

BRIEF DESCRIPTION OF THE DRAWINGS

Various aspects of this disclosure may be better understood upon reading the following detailed description and upon reference to the drawings in which.

DETAILED DESCRIPTION

Figure 1:
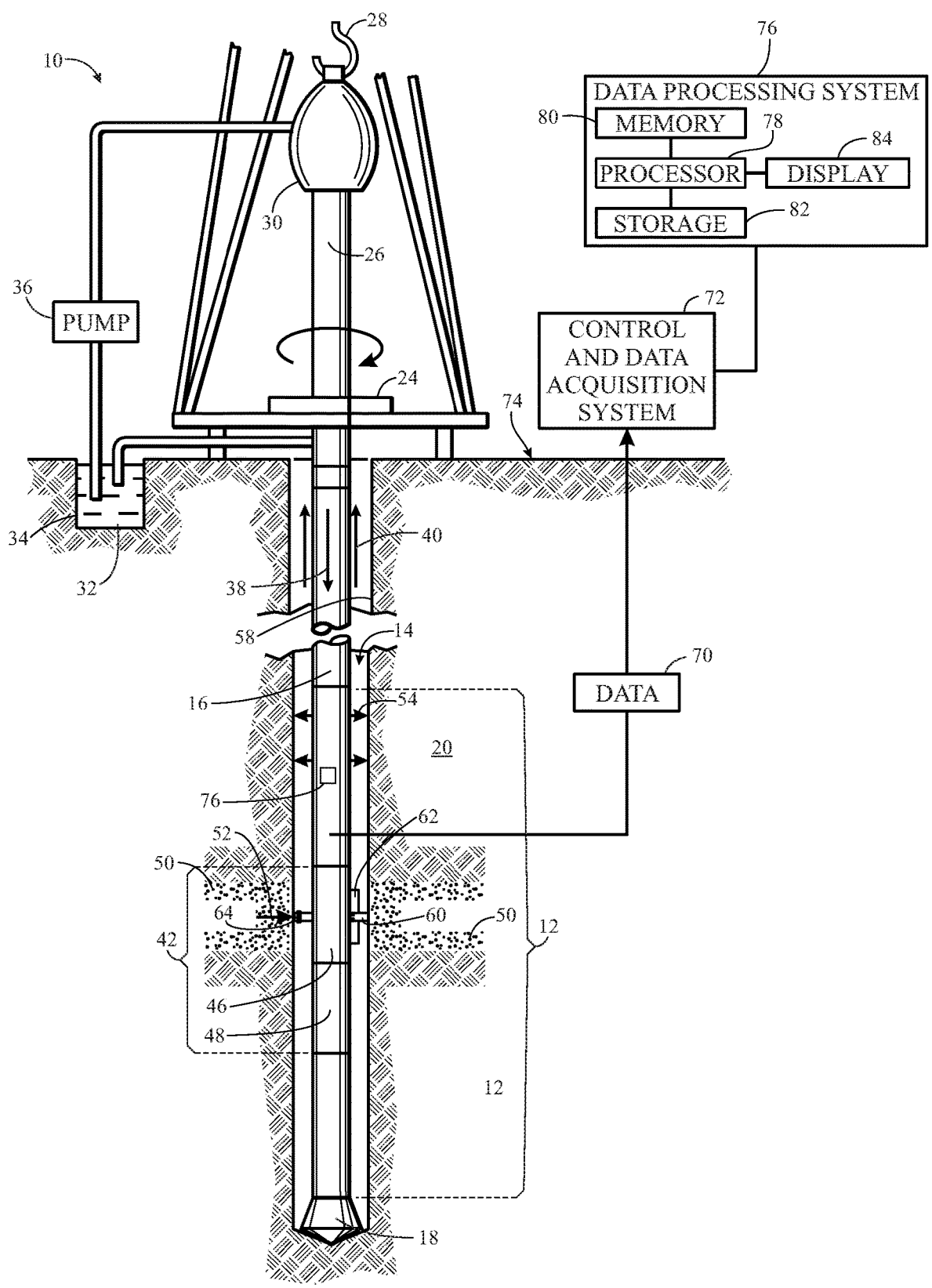
FIG. 1 is a schematic diagram of a wellsite system that may employ downhole fluid analysis methods for determining oil base mud contamination in a formation fluid, in accordance with an embodiment.

One or more specific embodiments of the present disclosure will be described below. These described embodiments are examples of the presently disclosed techniques. Additionally, in an effort to provide a concise description of these embodiments, features of an actual implementation may not be described in the specification. It should be appreciated that in the development of any such actual implementation, as in any engineering or design project, numerous implementation-specific decisions may be made to achieve the developers' specific goals, such as compliance with system-related and business-related constraints, which may vary from one implementation to another. Moreover, it should be appreciated that such a development effort might be complex and time consuming, but would still be a routine undertaking of design, fabrication, and manufacture for those of ordinary skill having the benefit of this disclosure.

When introducing elements of various embodiments of the present disclosure, the articles "a," "an," and "the" are intended to mean that there are one or more of the elements. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features.

Acquisition and analysis of representative formation fluid samples downhole in delayed or real time may be useful for determining the economic value of hydrocarbon reserves and oil field development. However, formation fluid samples may be contaminated with drilling fluids that penetrate the geological formation during and/or after drilling operations. As such, it may be difficult to assess a composition of the geological formation fluid (also referred to as "native formation fluid") and determine the economic value of the hydrocarbon reserves. For example, native formation fluids, such as gas and oil, may be miscible with the drilling fluid (e.g., oil-based mud filtrate), thereby affecting sample quality and analysis. Downhole acquisition tools may acquire formation fluid (e.g., drilling mud contaminated formation fluid or uncontaminated/native formation fluid) and test the formation fluid to determine and/or estimate an amount of oil-based mud filtrate in the formation fluid. This may be referred to as oil contamination monitoring (OCM). Based on the amount of oil-based mud filtrate in the formation fluid, an operator of the downhole acquisition tool may determine when the formation fluid is representative of uncontaminated native reservoir fluid. In this way, the fluid properties and composition of the native reservoir fluid may be analyzed to determine the economic value of the hydrocarbon reserve. In addition, monitoring oil-based mud contamination downhole, e.g., in real time, avoids delays associated with fluid analysis at surface or at a remote location (e.g., offsite laboratory), thereby decreasing the overall operational costs of wellbore drilling operations.

Downhole acquisition tools such as wellbore formation testers (WFT) may perform downhole fluid analysis to acquire, monitor, and analyze the formation fluid (e.g., contaminated and uncontaminated formation fluids) downhole. In some cases, this may be carried out in real time. Downhole fluid analysis allows the formation fluid to be analyzed under wellbore conditions (e.g., pressure and temperature), thereby providing a better indication of the volume and composition of the formation fluid compared to surface analysis techniques, which may be unable to maintain the formation fluid at wellbore pressures and temperatures. As such, the fluid properties and/or composition of the formation fluid may change at surface (e.g., at standard pressure and temperature) due, in part, to volatility of certain hydrocarbons (e.g., methane ($C_1$), ethane ($C_2$), propane ($C_3$), butane ($C_4$), pentane ($C_5$)) at surface conditions and changes in formation fluid volume.

The downhole acquisition tools include multiple sensors that measure fluid properties, such as gas-to-oil ratio (GOR), mass density, optical density (OD) at multiple optical channels, compositions of carbon dioxide ($CO_2$), $C_1$, $C_2$, $C_3$, $C_4$, $C_5$, and $C_{6+}$, formation volume factor, viscosity, resistivity, fluorescence, and others in, for example, real time. The measured fluid properties may be used to determine and/or estimate (e.g., predict) an amount of the oil-based mud filtrate contamination in the formation fluid. For example, differences in the fluid properties between the native reservoir fluid (e.g., uncontaminated reservoir fluid) and pure oil-based mud filtrate may be used to monitor and quantify oil-based mud filtrate contamination of the formation fluid. However, the fluid properties of the native formation fluid and the pure oil-based mud filtrate are difficult to measure directly. As discussed above, the oil-based mud penetrates the geological formation during drilling, thereby mixing with the native formation fluid before drilling fluid analysis. Additionally, the oil-based mud used during drilling operations is generally reused between wells. Accordingly, the fluid properties of the native formation fluid and the pure oil-based mud are generally not available.

The systems and methods of this disclosure may increase the accuracy of oil-based mud filtrate contamination in formation fluids may be advantageous for operators to determine whether to proceed with or abandon hydrocarbon recovery for a given wellbore. Accordingly, present embodiments include techniques that combine data from the multiple sensors of the downhole acquisition tool to improve quantification and estimation accuracy of oil-based mud filtrate contamination. In particular, the disclosed embodiments use a relationship between mass fraction composition data and volume fraction fluid property data of the contaminated formation fluid, the native formation fluid, and pure oil-based mud filtrate to quantify an amount of oil-based mud contamination downhole.

Figure 2:
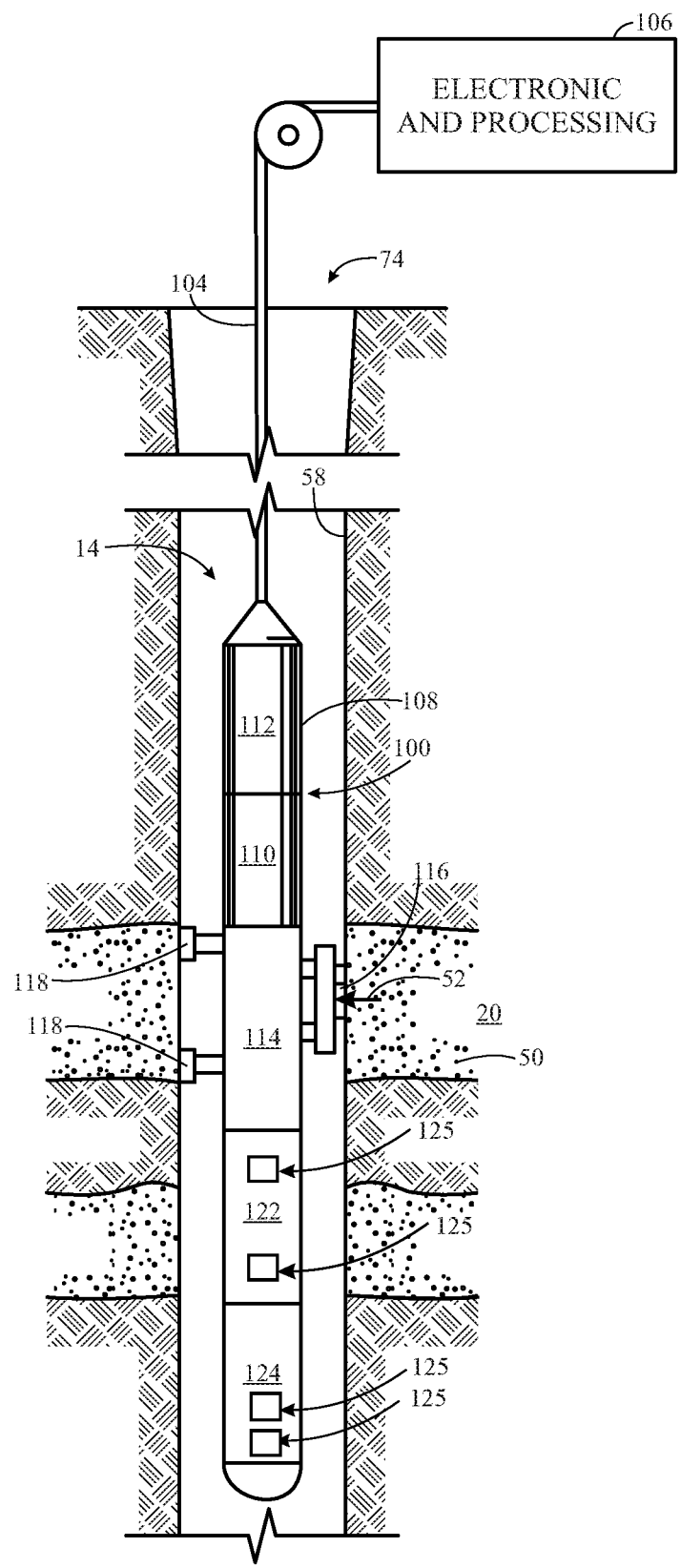
FIG. 2 is a schematic diagram of another embodiment of a wellsite system that may employ downhole fluid analysis methods for determining oil base mud contamination in a formation fluid, in accordance with an embodiment.

FIGS. 1 and 2 depict examples of wellsite systems that may employ the fluid analysis systems and techniques described herein. FIG. 1 depicts a rig 10 with a downhole tool 12 suspended therefrom and into a wellbore 14 via a drill string 16. The downhole tool 12 has a drill bit 18 at its lower end thereof that is used to advance the downhole tool 12 into geological formation 20 and form the wellbore 14. The drill string 16 is rotated by a rotary table 24, energized by means not shown, which engages a kelly 26 at the upper end of the drill string 16. The drill string 16 is suspended from a hook 28, attached to a traveling block (also not shown), through the kelly 26 and a rotary swivel 30 that permits rotation of the drill string 16 relative to the hook 28. The rig 10 is depicted as a land-based platform and derrick assembly used to form the wellbore 14 by rotary drilling. However, in other embodiments, the rig 10 may be an offshore platform.

Drilling fluid or mud 32 (e.g., oil base mud (OBM)) is stored in a pit 34 formed at the well site. A pump 36 delivers the drilling fluid 32 to the interior of the drill string 16 via a port in the swivel 30, inducing the drilling mud 32 to flow downwardly through the drill string 16 as indicated by a directional arrow 38. The drilling fluid exits the drill string 16 via ports in the drill bit 18, and then circulates upwardly through the region between the outside of the drill string 16 and the wall of the wellbore 14, called the annulus, as indicated by directional arrows 40. The drilling mud 32 lubricates the drill bit 18 and carries formation cuttings up to the surface as it is returned to the pit 34 for recirculation.

The downhole acquisition tool 12, sometimes referred to as a bottom hole assembly ("BHA"), may be positioned near the drill bit 18 and includes various components with capabilities, such as measuring, processing, and storing information, as well as communicating with the surface. A telemetry device (not shown) also may be provided for communicating with a surface unit (not shown). As should be noted, the downhole tool 12 may be conveyed on wired drill pipe, a combination of wired drill pipe and wireline, or other suitable types of conveyance.

The downhole acquisition tool 12 further includes a sampling system 42 including a fluid communication module 46 and a sampling module 48. The modules may be housed in a drill collar for performing various formation evaluation functions, such as pressure testing and fluid sampling, among others. As shown in FIG. 1, the fluid communication module 46 is positioned adjacent the sampling module 48; however the position of the fluid communication module 46, as well as other modules, may vary in other embodiments. Additional devices, such as pumps, gauges, sensor, monitors or other devices usable in downhole sampling and/or testing also may be provided. The additional devices may be incorporated into modules 46, 48 or disposed within separate modules included within the sampling system 42.

In certain embodiments, the downhole acquisition tool 12 may evaluate fluid properties of the drilling mud 32, native formation fluid 50, and/or a contaminated formation fluid, as illustrated by arrow 52. Accordingly, the sampling system 42 may include sensors that may measure fluid properties such as gas-to-oil ratio (GOR), mass density, optical density (OD), composition of carbon dioxide ($CO_2$), $C_1$, $C_2$, $C_3$, $C_4$, $C_5$, and $C_{6+}$, formation volume factor, viscosity, resistivity, fluorescence, and combinations thereof of the drilling mud 32, native formation fluid 50, and formation fluid 52. As should be noted, the formation fluid 52 may be the drilling mud 32, the native formation fluid 50, or a mixture of the drilling mud 32 and the native formation fluid 50). For example, during drilling, the drilling mud 32 may penetrate wellbore wall 58, as illustrated by arrow 54, thereby contaminating the native formation fluid 50. Therefore, as discussed in further detail below, the sampling system 42 may be used for oil contamination monitoring (OCM) to determine an amount of the drilling mud filtrate 54 (e.g., oil based mud filtrate) in the formation fluid 52 (e.g., the drilling mud 32, the native formation fluid 50, or a combination thereof).

The fluid communication module 46 includes a probe 60, which may be positioned in a stabilizer blade or rib 62. The probe 60 includes one or more inlets for receiving the formation fluid 52 and one or more flow lines (not shown) extending into the downhole tool 12 for passing fluids (e.g., the formation fluid 52) through the tool. In certain embodiments, the probe 60 may include a single inlet designed to direct the formation fluid 52 into a flowline within the downhole tool 12. Further, in other embodiments, the probe 60 may include multiple inlets that may, for example, be used for focused sampling. In these embodiments, the probe 60 may be connected to a sampling flow line, as well as to guard flow lines. The probe 60 may be movable between extended and retracted positions for selectively engaging the wellbore wall 58 of the wellbore 14 and acquiring fluid samples from the geological formation 20. One or more setting pistons 64 may be provided to assist in positioning the fluid communication device against the wellbore wall 58.

The sensors within the sampling system 42 may collect and transmit data 70 associated with the fluid properties and the composition of the formation fluid 52 to a control and data acquisition system 72 at surface 74, where the data 70 may be stored and processed in a data processing system 76 of the control and data acquisition system 72.

The data processing system 76 may include a processor 78, memory 80, storage 82, and/or display 84. The memory 80 may include one or more tangible, non-transitory, machine readable media collectively storing one or more sets of instructions for operating the downhole acquisition tool 16 and estimating an amount of oil-based mud filtrate 54 (e.g., drilling mud 32) in the formation fluid 52. The memory 80 may store mixing rules and algorithms associated with the native formation fluid 50 (e.g., uncontaminated formation fluid), the drilling mud 32, and combinations thereof to facilitate estimating an amount of the drilling mud 32 in the formation fluid 52. The data processing system 76 may use the fluid property and composition information of the data 70 to estimate an amount of the oil-based mud contamination in the formation fluid 52, as discussed in further detail below with reference to FIG. 3. In certain embodiments, the data processing system 76 may apply filters to remove noise from the data 70. In addition, the data processing system 76 may select fluid property and composition data 70 that has enough contrast between the native formation fluid 50 and the pure oil-based mud 32. For example, certain fluid and compositional parameters between the native formation fluid 50 and the pure oil-based mud filtrate 54 (e.g., the drilling mud 32) may be similar, such that it may be difficult to differentiate between the two fluids. However, by selecting parameters that clearly differentiate the native formation fluid 50 and the pure oil-based mud filtrate 54, the quantification accuracy of the oil-based mud filtrate 54 contamination may be increased. By way of example, the data processing system 76 may select GOR, OD, density, shrinkage factor, weight fraction of $C_1$, and weight fraction of $C_{6+}$ to determine the amount of oil-based mud filtrate 54 contamination in the native formation fluid 50.

To process the data 70, the processor 78 may execute instructions stored in the memory 80 and/or storage 82. For example, the instructions may cause the processor to quantify the amount of oil-based mud filtrate 54 contamination in the formation fluid 52, and estimate fluid and compositional parameters of the native formation fluid 50 and the pure oil-based mud filtrate 54, as discussed in further detail below. As such, the memory 80 and/or storage 82 of the data processing system 76 may be any suitable article of manufacture that can store the instructions. By way of example, the memory 80 and/or the storage 82 may be ROM memory, random-access memory (RAM), flash memory, an optical storage medium, or a hard disk drive. The display 84 may be any suitable electronic display that can display information (e.g., logs, tables, cross-plots, etc.) relating to properties of the well as measured by the downhole acquisition tool 16. It should be appreciated that, although the data processing system 76 is shown by way of example as being located at the surface 74, the data processing system 76 may be located in the downhole acquisition tool 16. In such embodiments, some of the data 70 may be processed and stored downhole (e.g., within the wellbore 14), while some of the data 70 may be sent to the surface 74 (e.g., in real time).

FIG. 2 depicts an example of a wireline downhole tool 100 that may employ the systems and techniques described herein to monitor oil based mud contamination of the formation fluid 52. The downhole tool 100 is suspended in the wellbore 14 from the lower end of a multi-conductor cable 104 that is spooled on a winch at the surface 74. Similar to the downhole tool 12, the wireline downhole tool 100 may be conveyed on wired drill pipe, a combination of wired drill pipe and wireline, or other suitable types of conveyance. The cable 104 is communicatively coupled to an electronics and processing system 106. The downhole tool 100 includes an elongated body 108 that houses modules 110, 112, 114, 122, and 124, that provide various functionalities including fluid sampling, fluid testing, operational control, and communication, among others. For example, the modules 110 and 112 may provide additional functionality such as fluid analysis, resistivity measurements, operational control, communications, coring, and/or imaging, among others.

As shown in FIG. 2, the module 114 is a fluid communication module 114 that has a selectively extendable probe 116 and backup pistons 118 that are arranged on opposite sides of the elongated body 108. The extendable probe 116 is configured to selectively seal off or isolate selected portions of the wall 58 of the wellbore 14 to fluidly couple to the adjacent geological formation 20 and/or to draw fluid samples from the geological formation 20. The probe 116 may include a single inlet or multiple inlets designed for guarded or focused sampling. The native formation fluid 50 may be expelled to the wellbore through a port in the body 108 or the formation fluid 52, including the native formation fluid 50, may be sent to one or more fluid sampling modules 122 and 124. The fluid sampling modules 122 and 124 may include sample chambers that store the formation fluid 52. In the illustrated example, the electronics and processing system 106 and/or a downhole control system are configured to control the extendable probe assembly 116 and/or the drawing of a fluid sample from the geological formation 20 to enable analysis of the formation fluid 52 for oil based mud filtrate contamination, as discussed above. As shown in the illustrated embodiments, the modules 122 and 124 may include a plurality of sensors 125 that are configured to analyze fluid from the geological formation to determine one or more properties of the fluid.

Figure 3:
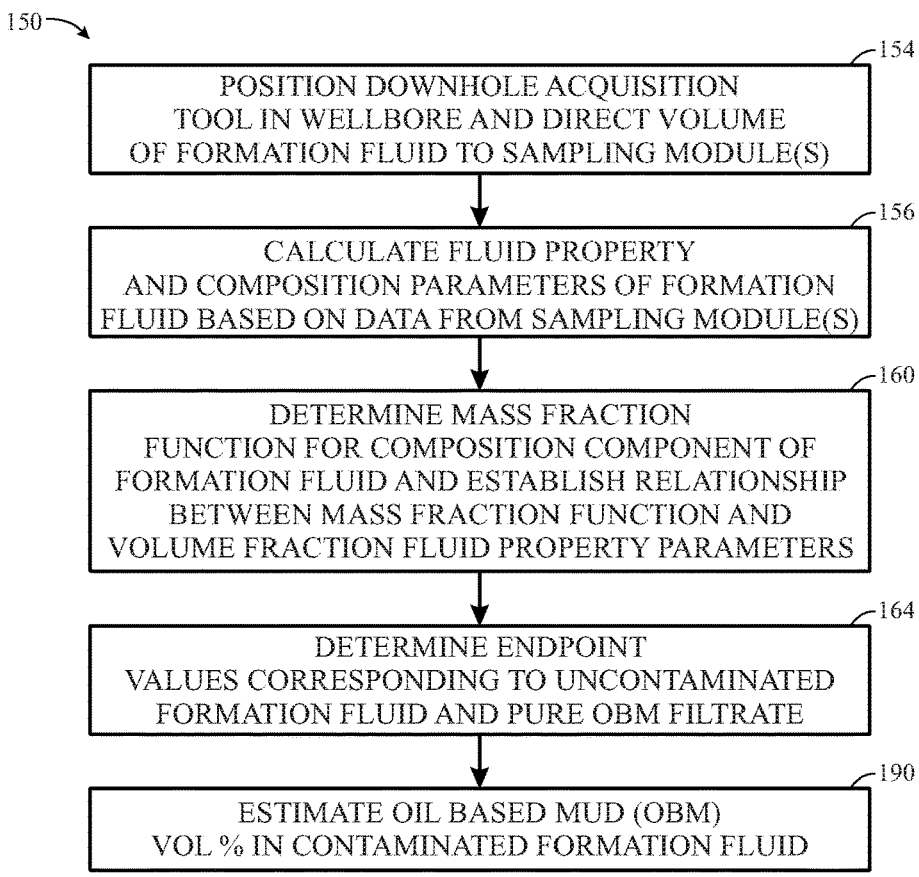
FIG. 3 is a flowchart of a method for using the downhole acquisition tool system of FIG. 1 to estimate oil-based mud contamination in a native reservoir fluid, in accordance with an embodiment.

A method for monitoring the oil-based mud contamination in the formation fluid 52 is illustrated in flowchart 150 of FIG. 3. For example, in the illustrated flowchart 150, the downhole acquisition tool 16 is positioned at a desired depth within the wellbore 14 and a volume of the formation fluid 52 is directed to the sampling modules (e.g., modules 48, 122, 124) for analysis (block 154). For example, the downhole acquisition tool 16 is lowered into the wellbore 14, as discussed above, such that the probe 60, 116 is within a fluid sampling region of interest. The probe 60, 116 faces toward the geological formation 20 to enable a flow of the formation fluid 52 through the flowline toward the sampling modules 48, 122, 124.

While in the downhole acquisition tool 16, the multiple sensors 125 detect and transmit fluid and compositional parameters (e.g., the data 70) of the formation fluid 52 such as, but not limited to, GOR, density ($\rho$), composition (mj), optical density (OD), shrinkage factor (b), and any other suitable parameter of the formation fluid 52 to the data processing system 76. The data processing system 76 applies one or more algorithms to calculate the fluid property and the composition (e.g., amount of $C_{1-6+}$) of the formation fluid 52 based on the data 70 (block 156). For example, the data processing system 76 may calculate the fluid and the compositional parameters based on mixing rule algorithms derived for binary fluids, such as the oil-based mud contaminated formation fluid, as described in further detail below.

For the purpose of the following discussions, it is assumed that an oil-based mud contaminated formation fluid is in a single-phase (e.g., liquid or gas) at downhole conditions due to the miscibility of the oil-based mud 32 and the hydrocarbon (e.g., oil and/or gas) present in the native formation fluid 50. Additionally, it is assumed that the oil-based mud filtrate 54 is present in flashed stock-tank oil (STO) phase and is not present in flashed gas phase when the native formation fluid 50 is flashed from downhole conditions to standard temperature and pressure conditions (e.g., surface conditions of approximately 0.1 megapascals (MPa) and approximately 15° C.). Accordingly, the following single phase mixing rules are defined for optical density (OD), EQ. 1; shrinkage factor (b), EQ. 2; $f$-function (e.g., auxiliary function for modified GOR), EQ. 3; density (ρ), EQ. 4; and composition mass fraction ($m_j$), EQ. 5.

$$OD_i = v_{obm} OD_{obmi} + (1 - v_{obm}) OD_{0i} \quad (EQ.\ 1)$$

$$b = v_{obm} b_{obm} + (1 - v_{obm}) b_0 \quad (EQ.\ 2)$$

$$f = v_{obm} f_{obm} + (1 - v_{obm}) f_0 \quad (EQ.\ 3)$$

$$\rho = v_{obm} \rho_{obm} + (1 - v_{obm}) \rho_0 \quad (EQ.\ 4)$$

$$m_j = w_{obm} m_{obmj} + (1 - w_{obm}) m_{0j} \quad (EQ.5)$$

where $v_{obm}$ and $w_{obm}$ are the oil-based mud filtrate 54 contamination level of the formation fluid 52 in volume fraction and weight fraction based on live fluid, respectively. The subscripts 0, obm, i, and j represent the uncontaminated formation fluid (e.g., the native formation fluid 50), pure oil-based mud filtrate 54, optical channel i, and component j in the formation fluid 52, respectively. As should be noted, j can refer to any component measured downhole. By way of example, $m_j$ may be the mass fraction $CO_2$, $C_1$, $C_2$, $C_3$-$C_5$, $C_{6+}$ (e.g., hexanes, heptanes, octanes, asphaltenes, etc.), or any other downhole component of interest in the formation fluid 52.

Using the composition (e.g., $m_j$) of the formation fluid 52 in combination with the fluid properties (e.g., optical density (OD), shrinkage factor, GOR, and density) to estimate an amount of the oil-based mud filtrate 54 contamination may provide a more robust and reliable quantification of the oil-based mud filtrate 54 for oil contamination monitoring (OCM) applications. As such, assessment of the native formation fluid 50 properties (e.g., uncontaminated formation fluid) may be obtained with a higher degree of confidence compared to existing techniques, which may be limited to OD parameters and probe type (e.g., focused, unfocused, unfocused 3D, etc.) used for sampling of the formation fluid 52. However, fluid composition, which is expressed as a mass fraction, and fluid properties, which are expressed in volume fraction, generally have a non-linear relationship. Therefore, it may be difficult to combine fluid property data with composition data for the purpose of oil contamination monitoring (OCM) and analysis. Accordingly, before discussing the use of the composition and fluid property data used for OCM, a discussion of a manner to establish a linear relationship between composition and fluid property parameters using novel auxiliary functions is presented.

As discussed above, the composition mass fraction equation ($m_j$) EQ. 5 may be used to obtain an amount (mass fraction) of a downhole component (e.g., $CO_2$, $C_1$, $C_2$, $C_3$-$C_5$, $C_{6+}$) present in the formation fluid 52. To establish a linear relationship between the composition and fluid property parameters, EQ. 5 may be rewritten, as shown below in EQ. 6. Using EQ. 6 and the density of the oil-based mud contaminated formation fluid (ρ) and the pure oil-based mud filtrate 54 ($\rho_{obm}$), the weight fraction ($w_{obm}$) for the pure oil-based mud filtrate 54 may be converted to a volume fraction ($v_{obm}$), as shown below in EQ. 7.

$$w_{obm} = (m_{0j} - m_j)/(m_{0j} - m_{obmj}) \quad (EQ.\ 6)$$

$$v_{obm} = \frac{w_{obm}\rho}{\rho_{obm}} = \frac{\rho}{\rho_{obm}} \frac{m_{0j} - m_j}{m_{0j} - m_{obmj}} \quad (EQ.\ 7)$$

EQ. 7 may be used to establish a relationship between the various other contamination volume fraction fluid property mixing rules such as EQ. 1-4. Accordingly, the method further includes determining a composition mass fraction function (hereinafter referred to as a "q-function") for the compositional parameter of the formation fluid 52 to establish a relationship with the fluid property parameters in EQ. 1-4 (block 160). By establishing a relationship between the mass fraction composition property and the contamination volume fraction, similar mixing rules for both the composition mass fraction and other fluid properties may be maintained. For example, in certain embodiments, the relationship between the q-function (e.g., the mass fraction function) and the contamination volume fraction mixing rules is linear. In other embodiments, the relationship between the q-function and the volume fraction mixing rules may be second order, third order, or more. Based on the volume fraction ($v_{obm}$) EQ. 7, the q-function ($q_j$) may be defined for quantification of the component j in the formation fluid 52, as shown below in EQ. 8. It should be noted that EQ. 8 has the same dimensions as m, which is referred to as a modified composition in weight fraction. For example, the q-function for an uncontaminated formation fluid is $q_{0j} = m_{0j}$ because the term $(m_{0j} - m_j)/(\rho/\rho_{obm})$ corresponding to the oil-based mud filtrate 54 contamination in the uncontaminated formation fluid is 0. Similarly, the q-function for the pure oil-based mud filtrate 54 is $q_{obm} = m_{obmj}$ because the density ratio of the oil-based mud contaminated formation fluid to the pure oil-based mud filtrate 54 ($\rho/\rho_{obm}$) is equal to $\rho_{obm}/\rho_{obm}$, which is equal to one (1). Therefore, EQ. 7 may be rewritten as shown in EQ. 9, and the mixing rule of the q-function may be expressed as shown in EQ. 10, thereby establishing a linear relationship between the contamination volume fraction and fluid property parameters in EQ. 1-4 and the mass fraction composition parameter in EQ. 5.

$$q_j = m_{0j} - (m_{0j} - m_j)\frac{\rho}{\rho_{obm}} \quad (EQ.\ 8)$$

$$v_{obm} = (q_{0j} - q_j)/(q_{0j} - q_{obmj}) \quad (EQ.\ 9)$$

$$q_j = v_{obm} q_{obmj} + (1 - v_{obm}) q_{0j} \quad (EQ.\ 10)$$

Based on the linear relationship established between the mixing rules for the fluid properties (e.g., EQ. 1-4) and the composition (e.g., EQ. 8-10), the volume fraction of the oil-based mud filtrate 54 contamination in the formation fluid 52 may be expressed as follows:

$$v_{obm} = \frac{OD_{0i} + OD_i}{OD_{0i} - OD_{obmi}} \quad (EQ.\ 11)$$

$$= \frac{f_o - f}{f_o - f_{obm}}$$

$$= \frac{b_o - b}{b_o - b_{obm}}$$

$$= \frac{\rho_o - \rho}{\rho_o - \rho_{obm}}$$

$$= \frac{q_{oj} - q_j}{q_{oj} - q_{obmj}}$$

where the subscripts 0, obm, i, and j are the uncontaminated formation fluid (e.g., the native formation fluid 50), pure oil-based mud filtrate 54, optical channel i, and component j in the formation fluid 52, respectively, and the symbols without any subscripts are the fluid properties of the contaminated formation fluid, which are measured downhole (e.g., in real time). Derivation of the OD, $f$-function, shrinkage (b), and density ($\rho$) parameters in EQ. 12 are described in U.S. patent application Ser. No. 14/177,744 and U.S. Publication No. 2014/0316705 assigned to Schlumberger Technology Corporation, and are hereby incorporated by reference in their entirety.

Based on the linear relationship between the fluid property and the compositional parameters of the formation fluid 52, EQ. 11 may be used to estimate oil-based mud filtrate 54 contamination. However, prior to estimating the oil-based mud filtrate 54 contamination, the native formation fluid 50 and the pure oil-based mud filtrate 54 (e.g., endpoints) properties (e.g., fluid and compositional properties) may need to be determined. Accordingly, the method 150 includes determining endpoint values corresponding to the native formation fluid 50 and the pure oil-based mud filtrate 54 (block 164). For example, in certain embodiments, reliable and accurate endpoints may be obtained by the linear relationship between the composition q-function (e.g., EQ. 10) and at least one of the fluid property parameters (e.g., EQ. 1-4). The fluid properties ($OD_i$, $f$-function, shrinkage factor (b), density ($\rho$), and $q_j$-function) change with a volume of fluid (e.g., the formation fluid 52) pumped into the flowline of the downhole acquisition tool 16 over time. That is, a concentration of oil-based mud filtrate 54 in the formation fluid 52 may decrease over time as the native formation fluid 50 continues to flow from the geological formation 20 into the wellbore 14 and through the flowline, thereby changing the overall composition and fluid properties of the formation fluid 52 (e.g., from oil-based mud contaminated formation fluid to the native formation fluid 50) measured in the sampling modules 48, 122, 124. Moreover, as shown in EQ. 12, any pair of $OD_i$, $f$-function, shrinkage factor (b), density ($\rho$), and $q_j$-function are mutually linearly related because the properties of the native formation fluid 50 and the pure oil-based mud filtrate 54 are unvaried (e.g., constant). As such, in certain embodiments, the data processing system 76 may establish cross plots among the fluid properties to verify the linear relationship between the $q_j$-function and one of the $OD_i$, $f$-function, shrinkage factor (b), and density ($\rho$) parameters of the formation fluid 52. In other embodiments, the data processing system 76 may apply a correlation coefficient to provide a degree of linearity between the $q_j$-function and any one of the fluid property parameters (e.g., $OD_i$, $f$-function, shrinkage factor (b), and density ($\rho$)). Exemplary cross-plots demonstrating the linear relationship between the novel q-function for $C_1$ and $C_{6+}$ fluid components and the $f$-function (e.g., GOR) for three distinct oil-based mud contaminated fluids are shown FIGS. 4-9 and described in further detail below.

Figure 4:
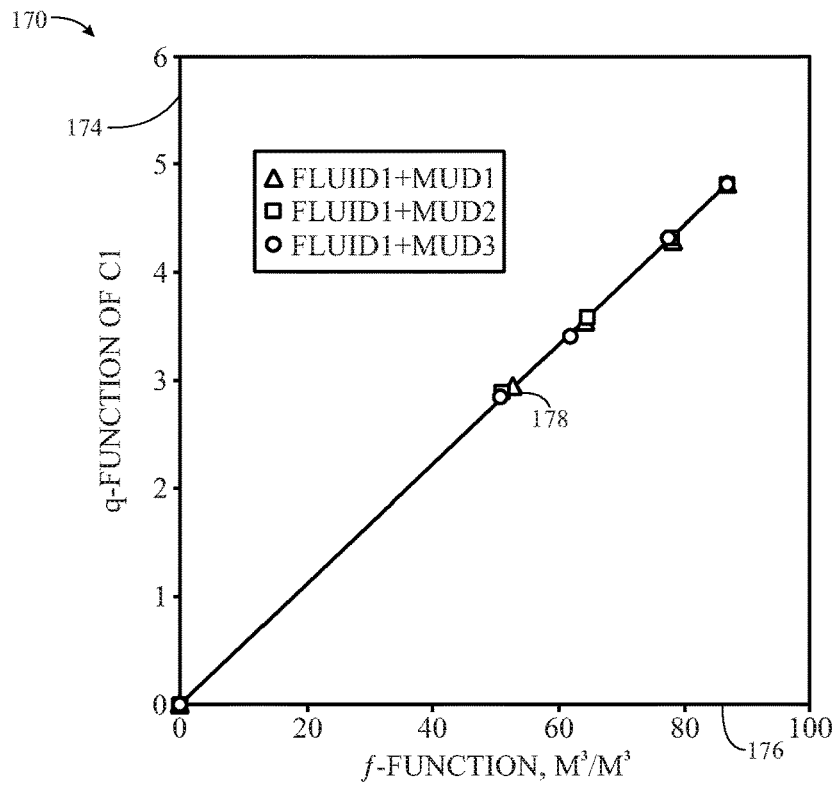
FIG. 4 is a plot of a relationship between a composition mass fraction function ("q-function") for $C_1$ and a gas-to-oil ratio (GOR) $f$-function for a first fluid and oil-based mud mixture, in accordance with an embodiment.
Figure 5:
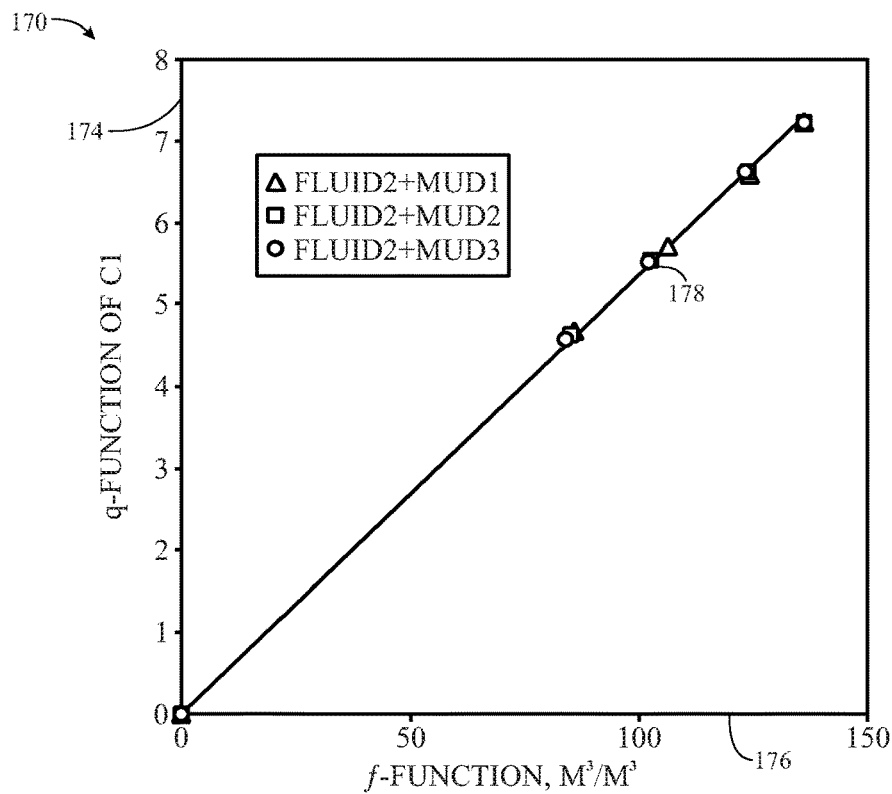
FIG. 5 is a plot of a relationship between a composition q-function for $C_1$ and a gas-to-oil ratio (GOR) $f$-function for a second fluid and oil-based mud mixture, in accordance with an embodiment.
Figure 6:
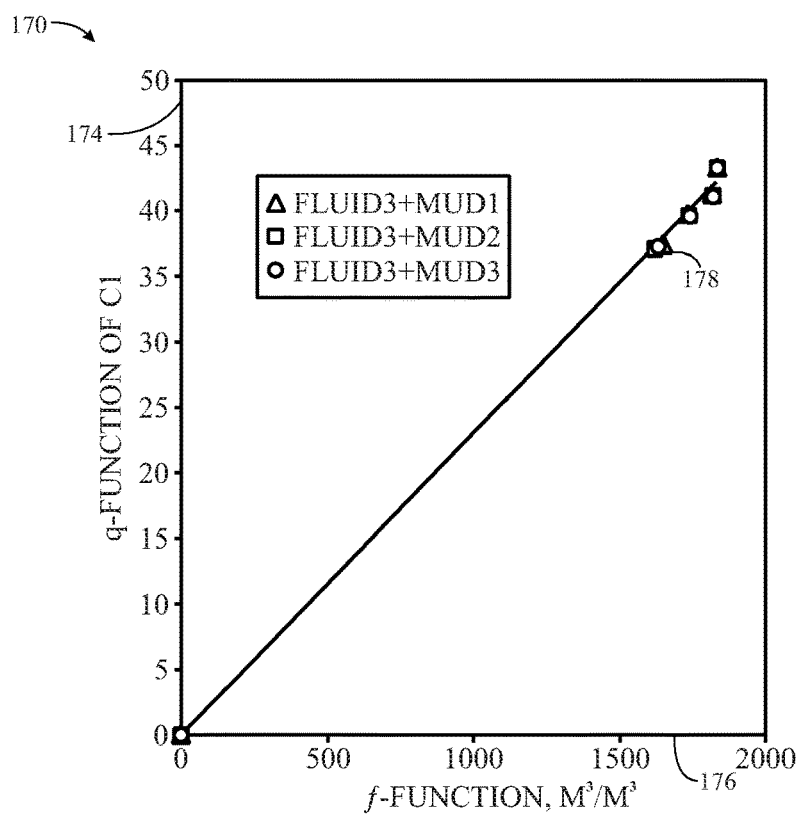
FIG. 6 is a plot of a relationship between a composition q-function for $C_1$ and a gas-to-oil ratio (GOR) $f$-function for a third fluid and oil-based mud mixture, in accordance with an embodiment.
Figure 7:
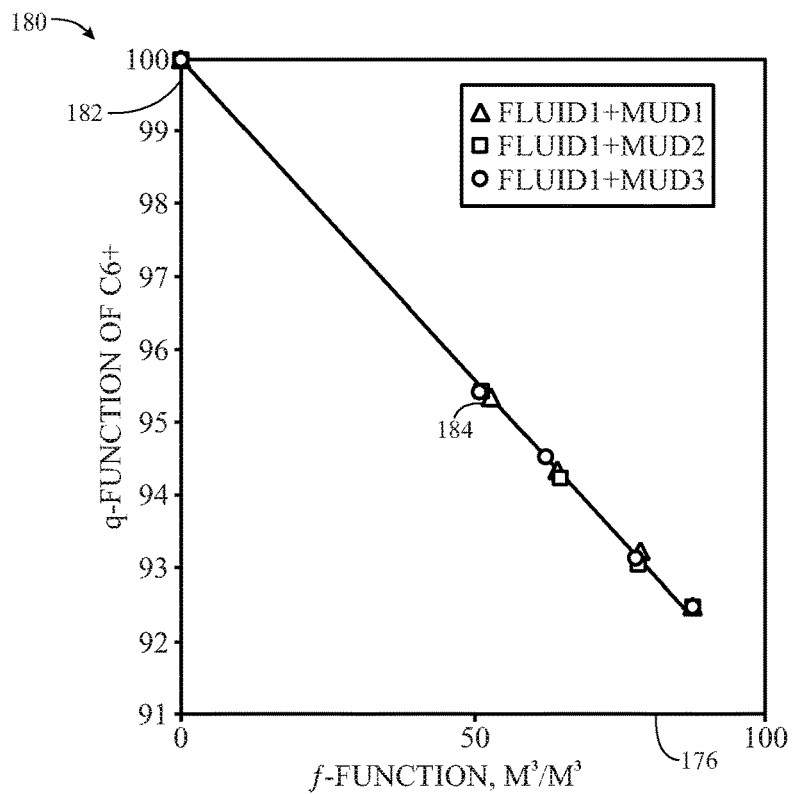
FIG. 7 is a plot of a relationship between a composition q-function for $C_{6+}$ and a gas-to-oil ratio (GOR) $f$-function for the first fluid and oil-based mud mixture, in accordance with an embodiment.
Figure 8:
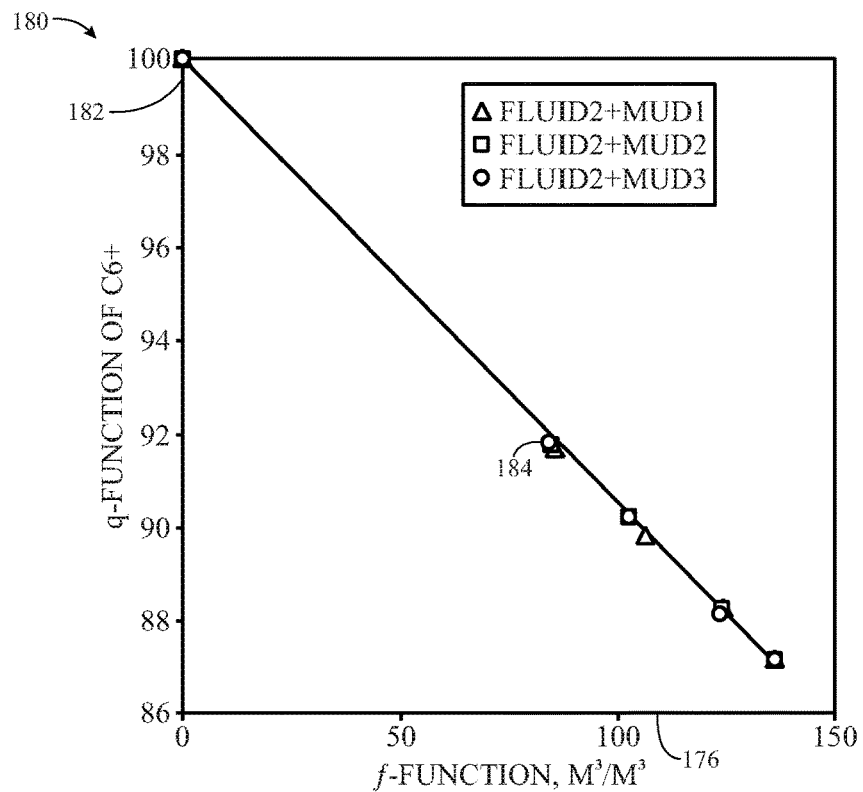
FIG. 8 is a plot of a relationship between a composition q-function for $C_{6+}$ and a gas-to-oil ratio (GOR) $f$-function for the second fluid and oil-based mud mixture, in accordance with an embodiment.
Figure 9:
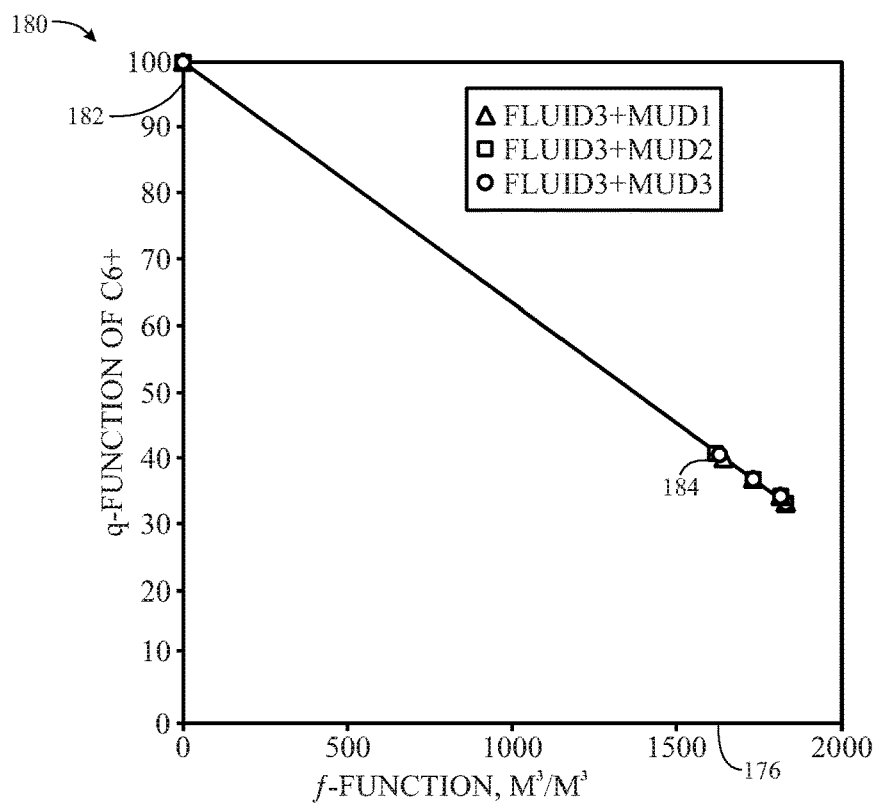
FIG. 9 is a plot of a relationship between a composition q-function for $C_{6+}$ and a gas-to-oil ratio (GOR) $f$-function for the third fluid and oil-based mud mixture, in accordance with an embodiment.

FIGS. 4-9 show cross-plots 170 of the example cases of three different oil-based mud contaminated fluid showing a linear relationship between the novel q-function and the $f$-function mixing rules discussed above. For example, FIGS. 4-6 illustrate cross-plots 170 for q-function for $C_1$ 174 vs. $f$-function 176 for example fluids 1-3, respectively, each contaminated with different oil-based muds. As shown, the cross-plots 170 data points 178 for each respective fluid are linear, thereby verifying the linear relationship between the q-function for $C_1$ and the $f$-function (e.g., GOR). Notably, the cross-plot 170 also illustrates the reliability of the data points 178 for each respective example fluid. Similarly, FIGS. 7-9 illustrate cross-plots 180 for q-function for $C_{6+}$ 182 vs. $f$-function 176 showing a linear relationship between the data points 184 for each respective example fluid 1-3. Therefore, based on the data provided in the example cross-plots 170, 180, the linear relationship between the novel q-function for composition components and the fluid property parameters is established. As such, the disclosed q-function for the fluid composition components may be used by the data processing system 76 to accurately and reliably estimate the oil-based mud contamination in the formation fluid 52 downhole, e.g., in real time. Consequently, the efficacy of OCM may be increased for the assessment of hydrocarbons in regions of interest within the wellbore 14.

Once the linearity between the q-function and the other fluid property parameters is established, the data processing system 76 may estimate the fluid property and compositional parameters for the native formation fluid 50 and the pure oil-based mud (e.g., the drilling mud 32/oil-based mud filtrate 54). For example, in certain embodiments, the data processing system 76 may extrapolate the values obtained from EQ. 12 to determine the q-function, $OD_i$, $f$-function, shrinkage factor (b), and density ($\rho$) of the native formation fluid 50 and the pure oil-based mud filtrate 54. Due to the linearity of the fluid property and composition parameters, robust and reliable endpoints (e.g., fluid and composition properties of the native formation fluid 50 and the pure oil-based mud filtrate 54) may be obtained. In particular, the fluid and compositional properties of the pure oil-based mud filtrate 54 may be obtained because it may be assumed that the pure oil-based mud filtrate 54 does not have GOR, methane ($C_1$), ethane ($C_2$), OD at color channels of interest, approximately 100% $C_{6+}$, or any combination thereof.

In certain embodiments, a large amount of oil-based mud 32 may penetrate the geological formation 20. As such, the initial flow of the formation fluid 52 flowing through the flowline may be essentially pure oil-based mud filtrate 54. Therefore, the fluid property parameters (e.g., OD, density, and other fluid properties) for the pure oil-based mud filtrate 54 in the initial flow of the formation fluid 52 into the flowline may be obtained at the start of drilling fluid analysis in the sampling modules 48, 122, 124. In other embodiments, the optical density (OD), density, and/or other measurable property of the pure oil-based mud filtrate 54 may be obtained during formation water sampling stations. For example, the geological formation water and the oil-based mud filtrate 54 separate due, in part, to slug flow and immiscibility of the geological formation water and the oil-based mud filtrate 54. As such, the fluid property parameters of the pure oil-based mud filtrate 54 and the geological formation water are clearly distinguished, thereby facilitating accurate and reliable fluid property and composition measurements for the pure oil-based mud filtrate 54. Consequently, once the fluid property and compositional parameters of the pure oil-based mud filtrate 54 are known, the mixing rules in EQ. 1-4 and 10 may be used to estimate the oil-based mud filtrate 54 contamination in the formation fluid 52.

In other embodiments, a power-law decay model for the filtrate contamination may be used to obtain the endpoint parameters for the native formation fluid 50. For example, the changing fluid properties over time and/or pumpout volume (e.g., volume of the mixed invaded/contaminated fluid and native formation fluid 50 pumped out of the geological formation 20 and into the wellbore 14 and the downhole acquisition tool 16) may be used to obtain native formation fluid 50 properties during cleanup. Power functions (e.g., exponential, asymptote, or other functions) may be used to fit the data (e.g., real time data) from the downhole fluid analysis to determine the fluid properties of the native formation fluid 50. Derivation of the power-law decay model is described in U.S. Patent Application Ser. No. 61/985,376 assigned to Schlumberger Technology Corporation and is hereby incorporated by reference in its entirety. By way of example, a power-law model for obtaining native formation fluid 50 and pure oil-based mud filtrate 54 fluid properties is expressed as:

$$v_{obm} = \frac{OD_{0i} + OD_i}{OD_{0i} - OD_{obmi}} \quad \text{(EQ. 12)}$$
$$= \frac{f_o - f}{f_o - f_{obm}}$$
$$= \frac{b_o - b}{b_o - b_{obm}}$$
$$= \frac{\rho_o - \rho}{\rho_o - \rho_{obm}}$$
$$= \frac{q_{oj} - q_j}{q_{oj} - q_{obmj}}$$
$$= \beta V^{-\gamma}$$

where

V is the volume of fluid pumped from the geological formation to the drilling fluid analysis γ is a parameter of the probe sampling β is an adjustable parameter In certain embodiments, the downhole acquisition tool 16 may be an unfocused probe sampling tool (e.g., a 3-D radial unfocused sampling tool or any other suitable unfocused probe sampling tool). Therefore, γ may be between approximately 5/12 and approximately 2/3 depending of the type of unfocused probe sampling tool and the flow regime. By way of example, γ may be approximately 5/12 for an intermediate flow regime and approximately 2/3 for a development flow region. The adjustable parameter, β, may be the difference in the fluid properties between the oil-based mud filtrate 54 and the native formation fluid 50. To determine the fluid properties of the native formation fluid 50, the volume V may be extrapolated to infinity for each desired fluid property and composition parameter. For example, for the composition parameter (e.g., q-function), the EQ. 12 may be expressed as follows:

$$q_j = q_{0j}\beta_j V^{-\gamma} = m_{0j}\beta_j V^{-\gamma} \quad \text{(EQ. 13)}$$

Figure 10:
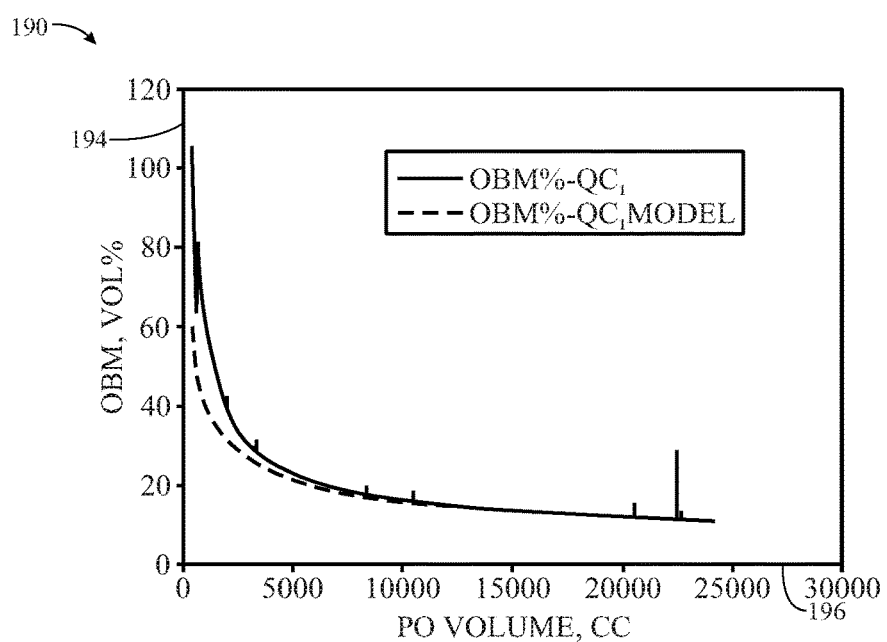
FIG. 10 is a plot of a relationship between a composition q-function for $C_1$ and a pumpout (PO) volume for cleanup data and modeled data using the q-function, in accordance with an embodiment.
Figure 11:
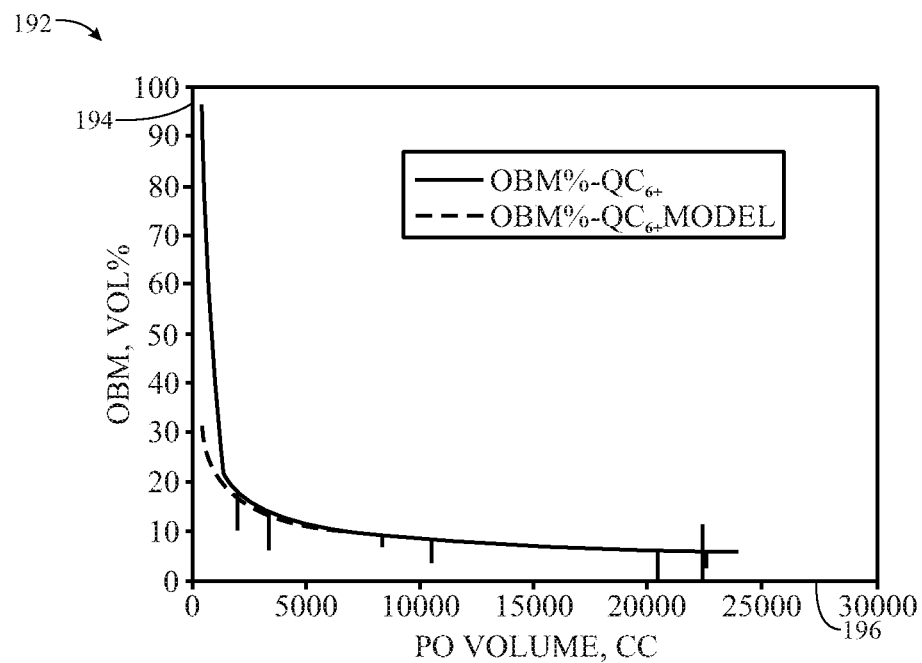
FIG. 11 is a plot of a relationship between a composition q-function for $C_{6+}$ and a PO volume for real-time downhole data and modeled data using the q-function, in accordance with an embodiment.

Fitting estimates obtained with EQ. 13 with the cleanup data from the downhole acquisition tool 16 may provide composition information for the native formation fluid 50 by extrapolating V to infinity. FIGS. 10-11 illustrate power-law fitting plots 190, 192 for oil-based mud, volume % 194 vs. pump out (PO) volume (cubic centimeters (cc)/milliliters (mL) 196 for both the model q-function (oil-based mud %-$qC_x$ model) and cleanup data (oil-based mud %-$qC_x$)). As shown, the modeled data estimated from the power-law fitting q-function model in EQ. 13 is well matched with the measured cleanup data for $C_1$ and $C_{6+}$ components.

Once the fluid property and compositional parameters of the native formation fluid 50 and the pure oil-based mud (e.g., the drilling mud 32/oil-based mud filtrate 54) have been established, as discussed above, the amount (e.g., % volume) of the oil-based mud filtrate 54 in the formation fluid 52 may be estimated (block 198) with a desirable degree of confidence. This is due, in part, to the measurement of the fluid properties and composition of the formation fluid 52 by different and independent sensors within the sampling modules 48, 122, 124, and the linearity of the parameters established by the mixing rules in EQ. 1-4 and 10. Accordingly, robust and consistent endpoints (e.g., pure oil-based mud 32, 54 and native formation fluid 50) may be obtained, and the oil-based mud filtrate 54 contamination in the formation fluid 52 may be accurately estimated based on the fluid properties and the mass fraction parameters of the formation fluid 52. Once an amount of the oil-based mud 32, 54 contamination in the formation fluid 52 is below a desired threshold, a sample of the formation fluid 52 may be collected and analyzed directly and continuously with the downhole acquisition tool 12, 100 to provide the fluid properties of the native formation fluid 50 without bringing the collected fluid sample (e.g., the native formation fluid 50) to the surface 74 for analysis.

A table of example cases, along with computed data for the amount of oil-based mud vol. %) in a fluid using the disclosed q-function, f-function, density (ρ), and shrinkage factor (b) is shown below. In the example cases, the measured lab value for the amount of oil-based mud present in an oil-based mud contaminated fluid case was compared to the amount of oil-based mud filtrate estimated using the mixing rules disclosed above (e.g., EQ. 11). As shown in Table 1, the estimated oil-based mud filtrate 54 determined using the q-function is consistent with the values obtained using the f-function, shrinkage factor (b), and the measured value obtained under a controlled laboratory environment. The estimated oil-based mud vol % across the multiple cases is reported in Table 1 below.

TABLE 1

Estimation of oil-based mud filtrate (vol. %) using different mixing rules

| | | oil-based mud, vol % | | | |
|---|---|---|---|---|---|
| | | Different Mixing Rules | | | |
| Case No. | Lab Value | q-Function ($C_1$) | q-Function ($C_{6+}$) | f-Function | Shrinkage Factor |
| Case 1 | 5.08 | 4.95 | 4.93 | 5.04 | 5.27 |
| Case 2 | 10 | 9.76 | 9.76 | 11.02 | 10.47 |
| Case 3 | 19.92 | 19.75 | 19.75 | 19.7 | 21.04 |

Figure 12:
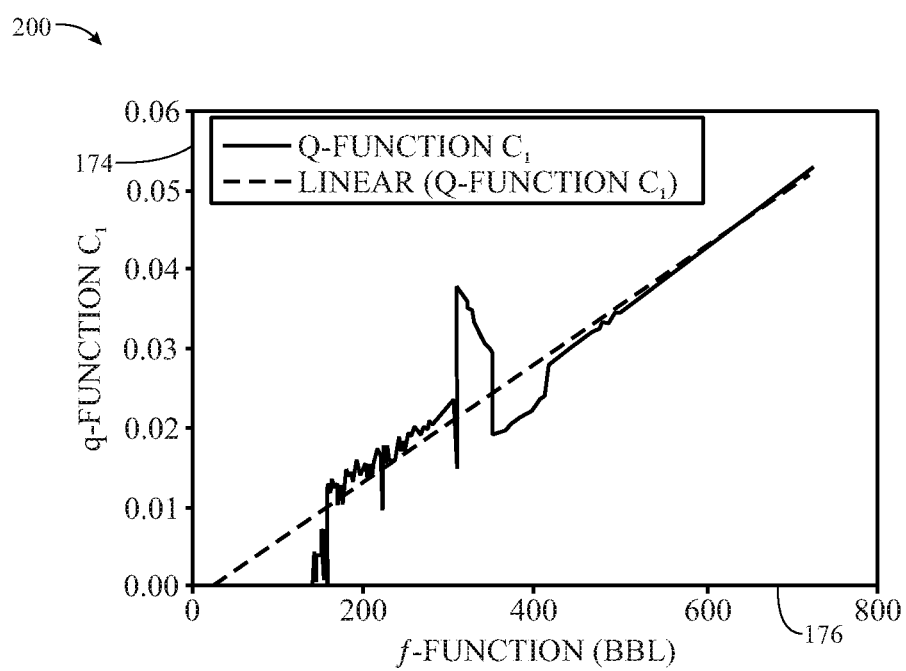
FIG. 12 is a plot of a relationship between a composition q-function for $C_1$ and a $f$-function for real-time downhole data and modeled data using the q-function, in accordance with an embodiment.
Figure 13:
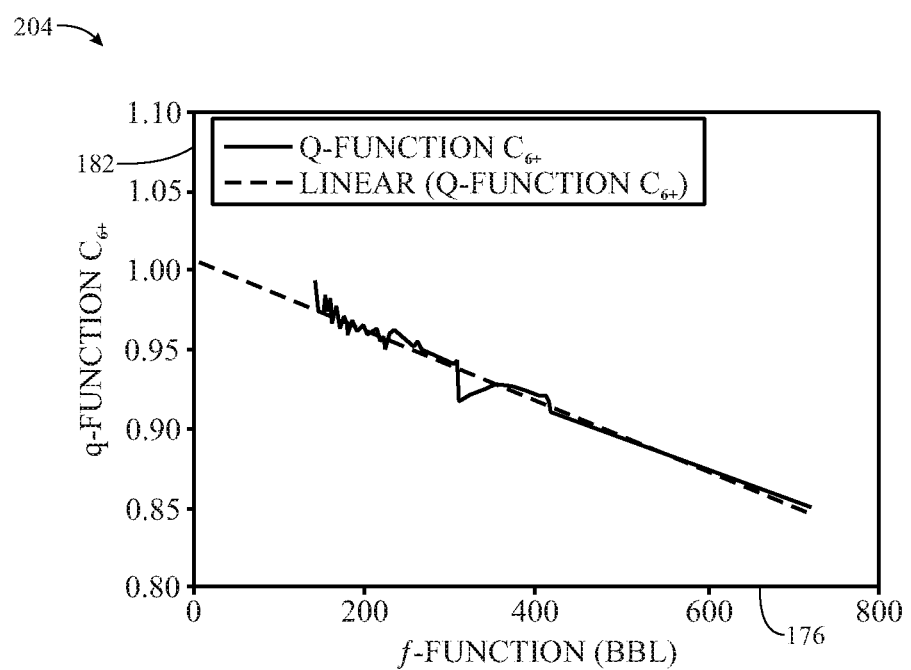
FIG. 13 is a plot of a relationship between a composition q-function for $C_{6+}$ and a $f$-function for real-time downhole data and modeled data using the q-function, in accordance with an embodiment.

Similarly, a table for example field cases, along with the computed values for the amount of the oil-based mud filtrate 54 in the formation fluid 52 is shown below in Table 2. In certain embodiments, the fluid property and compositional parameters for the native formation fluid 50 are determined based on the power-decay model in EQ. 12, and those of the pure oil-based mud filtrate 54 are determined from extrapolation of the mixing rule data cross-plots obtained from EQs. 1-4 and 10, such as those illustrated in FIGS. 4-9, or vice versa. In other embodiments, both the fluid property and compositional parameters of the native formation fluid 50 and the pure oil-based mud filtrate 54 are determined based on either the power-decay model or the mixing rule data cross-plots. Once the fluid property and composition parameters for the two endpoints (e.g., the native formation fluid 50 and the pure oil-based mud filtrate 54) are known, the amount of oil-based mud contamination (vol. %) may be determined based on the derived mixing rules according to EQ. 11. As shown in Table 2, the estimated parameters for the native formation fluid 50 using the power-law model in EQ. 12 and extrapolated from the linear relationship between the mixing rules disclosed above are consistent. Additionally, estimation of the oil-based mud filtrate 54 contamination using the disclosed q-function are also consistent with the oil-based mud filtrate 54 contamination estimated using the mixing rules derived for the OD, density (ρ), shrinkage factor (b), and ƒ-function. FIGS. 12 and 13 illustrate plots 200 and 204, respectively, illustrating a linear relationship between the disclosed q-function and the GOR ƒ-function for downhole data (e.g., real time data).

TABLE 2

Field Study Estimation of oil-based mud filtrate (vol. %) using mixing rules

| Property | OD[11] | Density, ρ (g/cm³) | Shrinkage Factor (b) | f-Function (scf/bbl) | q-Function ($C_1$) wt % | q-Function ($C_{6+}$) wt % |
|---|---|---|---|---|---|---|
| Native Fluid from Power-Law Fitting | 0.1633 | 0.6556 | 0.7085 | 680.06 | 6.9 | 88.15 |
| Native Fluid from Linear Relations | 0.1637 | 0.6563 | 0.7103 | | 6.85 | 88.1 |
| Mud Filtrate | 0.0665 | 0.7302 | 0.9177 | 0 | 0 | 97.28 |
| oil-based mud, vol % | 2 | 2.8 | 2.7 | 2.3 | 2.6 | 2 |

The estimated oil-based mud filtrate 54 contamination may be converted from volume fraction to weight fraction using EQ. 13 below to be consistent with standard reporting procedures for oil-based mud contamination.

$$w_{obmsto} = (v_{obmsto} \rho_{obmsto})/\rho_{sto} \quad (EQ.\ 13)$$

where
the subscripts sto and obmsto correspond to the stock-tank oil and the oil-based mud filtrate 54 in the stock-tank oil, respectively.

As shown above, the disclosed q-function provides a linear relationship between contamination volume fraction, composition mass fraction and other fluid property measurements for estimation of the oil-based mud contamination in the formation fluid 52. By applying the disclosed q-function to OCM algorithms, quantification accuracy for the oil-based mud contamination may be achieved. In addition, the intrinsic linear relationship between the multiple fluid property and composition parameters of the sampled formation fluid 52 may also provide useful information for quality assurance (QA) and quality control (QC) of the drilling fluid analysis measurements of the downhole acquisition tool 16. For example, in embodiments where the measurements derived from EQ. 11 are non-linear relative to one another, the data processing system 76 may indicate quality issues and alert an operator of the downhole acquisition tool 16, 100. Accordingly, the operator of the downhole acquisition tool 16, 100 may take appropriate action to provide a level of oil-based mud contamination of the formation fluid 52 within a suitable degree of accuracy. For example, in certain embodiments, the operator of the downhole acquisition tool 16, 100 may instruct the data processing system 76 to apply a correction factor to the data.

As discussed above, and shown in the data presented herein, the disclosed q-function for converting the contamination mass fraction associated with components j such as $CO_2$, $C_1$, $C_2$, $C_3$, $C_4$, $C_5$, and $C_{6+}$, among others, to contamination volume fraction, establishes a linear relationship with fluid property parameters used for OCM of formation fluids (e.g., the fluids 32, 50, 52). In addition, the disclosed q-function may be used to provide reliable and consistent estimation for native formation fluid 50 and pure oil-based mud filtrate 54 for drilling fluid analysis (e.g., in real time).

The specific embodiments described above have been shown by way of example, and it should be understood that these embodiments may be susceptible to various modifications and alternative forms. It should be further understood that the claims are not intended to be limited to the particular forms discloses, but rather to cover modifications, equivalents, and alternatives falling within the spirit of this disclosure.

The invention claimed is:

1. A method comprising: operating a downhole acquisition tool in a wellbore in a geological formation, wherein the wellbore or the geological formation, or both contains a first fluid that comprises a native reservoir fluid of the geological formation and a contaminant; receiving a portion of the first fluid into the downhole acquisition tool; determining a plurality of properties of the portion of the first fluid using the downhole acquisition tool, wherein the plurality of properties includes a mass fraction of a component of the portion of the first fluid and a density of the portion of the first fluid; and using a processor to estimate a volume fraction of the contaminant in the portion of the first fluid based at least in part on a composition mass fraction function that depends at least on the mass fraction of the component in the portion of the first fluid and the density of the portion of the first fluid.

2. The method of claim 1, wherein the composition mass fraction function depends at least on the mass fraction of the component in the portion of the first fluid, the density of the portion of the first fluid, an estimated mass fraction of the component in the native reservoir fluid, and a density of the contaminant.

3. The method of claim 2, comprising using the processor to determine the estimated mass fraction of the component in the native reservoir fluid based at least in part on one of the plurality of the properties of the portion of the first fluid other than the mass fraction of the component in the portion of the first fluid.

4. The method of claim 2, comprising using the processor to estimate a volume fraction of the contaminant in the portion of the first fluid based on an estimated mass fraction of the component in the contaminant, and using the processor to determine the estimated mass fraction of the component in the contaminant based at least in part on a plurality of properties of a previously obtained portion of the first fluid.

5. The method of claim 2, comprising using the processor to determine the estimated mass fraction of the component in the native reservoir fluid based at least in part on a volume fraction mixing rule that relates the composition mass fraction function to a second first fluid parameter, wherein the second first fluid parameter is based at least in part on a property of the plurality of properties of the portion of the first fluid other than the mass fraction of the component in the portion of the first fluid.

6. The method of claim 5, wherein the volume fraction mixing rule comprises a first expression that includes the composition mass fraction function that relates linearly to a second expression that includes the second first fluid parameter.

7. The method of claim 5, wherein the second first fluid parameter comprises a gas-to-oil ratio (GOR), shrinkage factor, a density, optical density, or a combination thereof.

8. The method of claim 2, comprising determining corresponding pluralities of properties for a plurality of other portions of the first fluid; and
using the processor to determine the estimated mass fraction of the component in the native reservoir fluid based at least in part on a plurality of values of the composition mass fraction function based on the properties for the plurality of other portions of the first fluid.

9. The method of claim 8, wherein the estimated mass fraction of the component in the native reservoir fluid is determined using a cross-plot of the plurality of values of the composition mass fraction function and a plurality of values of a second first fluid parameter, wherein the second first fluid parameter comprises a gas-to-oil ratio (GOR), shrinkage factor, a density, optical density, or a combination thereof.

10. The method of claim 1, wherein the composition mass fraction function accords with the following relationship:

$$q_j = m_{0j} \ (m_{0j} \ m_j) \frac{\rho}{\rho_{obm}}$$

where
$q_j$ represents the composition mass fraction function for the component in the portion of the first fluid;
$m_{0j}$ represents a mass fraction of the component j in the native reservoir fluid;
$m_j$ represents the mass fraction of the component j in the portion of the first fluid;
$\rho$ represents the density of the portion of the first fluid; and
$\rho_{obm}$ represents a density of the contaminant.

11. The method of claim 1, comprising obtaining a sample of the first fluid when the volume fraction of the contaminant in the portion of the first fluid is beneath a predetermined threshold.

12. A downhole fluid testing system comprising:
a downhole acquisition tool housing configured to be moved into a wellbore in a geological formation, wherein the wellbore or the geological formation, or both, contains first fluid that comprises a native reservoir fluid of the geological formation and a contaminant;
a plurality of sensors disposed in the downhole acquisition tool housing that are configured to analyze portions of the first fluid and obtain sets of properties of the portions of the first fluid, wherein each set of properties includes a mass fraction of a component of the portion of the first fluid and a density of the portion of the first fluid; and
a data processing system configured to estimate a volume fraction of the contaminant in at least one of the portions of the first fluid based at least in part on a composition mass fraction function that depends at least on the mass fraction of the component the at least one portion of the first fluid and the density of the at least one portion of the first fluid.

13. The system of claim 12, wherein the data processing system is disposed within the downhole acquisition tool housing, or outside the downhole acquisition tool housing at the surface, or both partly within the downhole acquisition tool housing and partly outside the downhole acquisition tool housing at the surface.

14. The system of claim 12, wherein the component of the portion of the first fluid comprises a carbon dioxide, a hydrocarbon, or a combination thereof.

15. The system of claim 12, wherein the component of the portion of the first fluid comprises a hydrocarbon that is found in the native reservoir fluid.

16. The system of claim 12, wherein the component of the portion of the first fluid comprises a C1 or C2 hydrocarbon, or both.

17. The system of claim 12, wherein the contaminant comprises an oil-based mud filtrate.

18. One or more tangible, non-transitory, machine-readable media comprising instructions to:
receive a plurality of fluid parameters of a portion of first fluid as analyzed by a downhole acquisition tool in a wellbore in a geological formation, wherein the wellbore or the geological formation, or both, contains the first fluid, wherein the first fluid comprises a mixture of native reservoir fluid of the geological formation and a contaminant, and wherein the plurality of fluid parameters includes a mass fraction of a component of the portion of the first fluid and a density of the portion of the first fluid; and
estimate a volume fraction of the contaminant in the portion of the first fluid based at least in part on a composition mass fraction function that depends at least on the mass fraction of the component in the portion of the first fluid and the density of the portion of the first fluid.

19. The one or more machine-readable media of claim 18, comprising instructions to estimate a mass fraction of the native reservoir fluid at least partly by relating the composition mass fraction function to a power function associated with one or more fluid properties other than the mass fraction of the component in the portion of the first fluid.

20. The one or more machine-readable media of claim 19, wherein the composition mass fraction function is related to the power function according to the following relationship:

$$q_j = m_{0j} - \beta_j V^{-\gamma}$$

where
$q_j$ represents the composition mass fraction function for the component j in the portion of the first fluid;
$m_{0j}$ represents the mass fraction of the component j in the native reservoir fluid;
$\beta_j$ represents a parameter based on the one or more fluid properties other than the mass fraction of the component in the portion of the first fluid;
V represents a volume of the portion of the first fluid; and
$\gamma$ represents a parameter representing a sampling rate of a probe used by the downhole acquisition tool.

* * * * *